US012290622B2

(12) United States Patent
Oishi et al.

(10) Patent No.: US 12,290,622 B2
(45) Date of Patent: May 6, 2025

(54) CLOSED CIRCULATION SYSTEM TEST APPARATUS FOR BLOOD PURIFICATION DEVICE USING WHOLE BLOOD

(71) Applicant: ASAHI KASEI MEDICAL CO., LTD., Tokyo (JP)

(72) Inventors: Teruhiko Oishi, Tokyo (JP); Hiroshi Umeno, Tokyo (JP); Hitomi Araki, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 478 days.

(21) Appl. No.: 17/915,700

(22) PCT Filed: Mar. 31, 2021

(86) PCT No.: PCT/JP2021/014056
§ 371 (c)(1),
(2) Date: Sep. 29, 2022

(87) PCT Pub. No.: WO2021/201181
PCT Pub. Date: Oct. 7, 2021

(65) Prior Publication Data
US 2023/0130941 A1  Apr. 27, 2023

(30) Foreign Application Priority Data
Mar. 31, 2020  (JP) ................................ 2020-064206

(51) Int. Cl.
*A61M 1/34*  (2006.01)
*A61M 1/16*  (2006.01)
(Continued)

(52) U.S. Cl.
CPC ........ *A61M 1/3434* (2014.02); *A61M 1/1603* (2014.02); *B01D 63/02* (2013.01); *A61M 1/3623* (2022.05)

(58) Field of Classification Search
CPC .............. A61M 1/3434; A61M 1/1603; A61M 1/3623; A61M 1/1615; A61M 1/341;
(Continued)

(56) References Cited

U.S. PATENT DOCUMENTS 5,700,372 A  12/1997  Takesawa et al.
5,711,883 A *  1/1998  Folden .................... A61M 1/16
73/40
(Continued)

FOREIGN PATENT DOCUMENTS

JP  2000-70360   3/2000
JP  2004-248844  9/2004
(Continued)

OTHER PUBLICATIONS

Extended European Search Report issued in EP Application No. 21780591.0, dated Aug. 10, 2023.
(Continued)

*Primary Examiner* — Philip R Wiest
*Assistant Examiner* — Brandon W. Levy
(74) *Attorney, Agent, or Firm* — GREENBLUM & BERNSTEIN, P.L.C.

(57) ABSTRACT

A closed circulation system test apparatus independently sets the amount of a liquid such as a dialysate for a blood purification device, facilitates management of operations of multiple pumps, and is capable of evaluating performance for removing wastes in blood and lifespan performance of membranes. The closed circulation system test apparatus includes: a blood sending line for sending blood from the blood bag to the blood purification device via a blood pump; a blood returning line for sending blood exiting from the blood purification device to the blood bag via a resistance imparting means; a filtrate line for sending the filtrate exiting from a dialysate outlet of the blood purification device to the
(Continued)

replacement fluid container via a filtrate pump; and a dialysate line for sending, via a dialysate pump, dialysate or replacement fluid from the replacement fluid container to a dialysate inlet of the blood purification device.

6 Claims, 2 Drawing Sheets

(51) Int. Cl.
*B01D 63/02* (2006.01)
*A61M 1/36* (2006.01)

(58) Field of Classification Search
CPC ........ A61M 2205/15; A61M 2205/705; A61M 2209/02; A61M 1/1613; A61M 1/3403; A61M 1/3437; A61M 1/3465; A61M 2205/70–707; A61M 1/1619; A61M 1/155; A61M 1/159; A61M 1/28; A61M 1/1656; A61M 1/167; A61M 2205/12; B01D 63/02; B01D 61/30; B01D 65/10
See application file for complete search history.

(56) References Cited

U.S. PATENT DOCUMENTS

| 2006/0157408 | A1 | 7/2006 | Kuroda et al. |
| 2008/0103427 | A1* | 5/2008 | Toyoda ............... A61M 1/361 |
| | | | 604/5.04 |
| 2011/0237997 | A1 | 9/2011 | Beden et al. |
| 2019/0099537 | A1* | 4/2019 | Barrett ................ B01D 61/22 |

FOREIGN PATENT DOCUMENTS

| JP | 2006-305333 | 11/2006 |
| JP | 2007-105262 | 4/2007 |
| JP | 2008-68129 | 3/2008 |
| JP | 2016-123711 | 7/2016 |
| JP | 2018-171431 | 11/2018 |

OTHER PUBLICATIONS

Hideki, K. et al., "Performance evaluation methods for blood purification devices", Journal of the Japanese Society for Dialysis Therapy 45(5), 2012, pp. 435-445.
International Search Report issued in International Patent Application No. PCT/JP2021/014056, dated Jun. 8, 2021.
Written Opinion issued in International Patent Application No. PCT/JP2021/014056, dated Sep. 29, 2022.
International Preliminary Report on Patentability issued in International Patent Application No. PCT/JP2021/014056, dated Jun. 8, 2021.

* cited by examiner

CLOSED CIRCULATION SYSTEM TEST APPARATUS FOR BLOOD PURIFICATION DEVICE USING WHOLE BLOOD

FIELD

The present invention relates to a closed circulation test apparatus for a blood purification device.

BACKGROUND

Serious patients with acute renal failure with rapidly reduced renal function accumulate water, urea, creatinine and $\beta_2$-microglobulin in the blood (hereunder referred to as "blood waste products"), and are therefore treated with continuous renal replacement therapy (CRRT) to remove the water in blood (hereunder referred to as "removed water"), whereby the blood waste products are removed. CRRT therapy includes continuous hemofiltration (CHF), continuous hemodialysis (CHD) and continuous hemofiltration dialysis (CHDF), with CHDF being further classified as pre-diluted or post-diluted depending on the location where the replacement fluid is added. With a continuous hemofiltration device (hereunder referred to simply as "hemofiltration device"), increasing the filtration volume and drainage volume generally increases the removal performance for blood waste products, but also increases the load on the membrane and shortens its life. It is therefore a goal to develop hemofiltration devices that have long membrane life even under conditions with increased filtration volume or drainage volume. However, no in vitro test apparatus or test method currently exists for in vitro testing that allows the fluid volume of dialysate, filtrate and replacement fluid (hereunder also referred to as "dialysate") to be freely set in each mode of CHF, CHD and CHDF (pre-dilution and post-dilution), and that allows "evaluation of removal performance for blood waste products" and "evaluation of membrane life performance" under conditions with increased drainage.

For example, NPL 1 describes a test method for evaluating the removal performance of blood waste products with a hemofiltration device, but because it is an evaluation method conducted in an open system in which the blood is in contact with the outside air, it is assumed that coagulation takes place more rapidly and thrombus formation tends to occur more readily on the membrane than under coagulation conditions in a closed system as used for actual patients, and this makes it impossible to accurately evaluate the lifetime performance of the membrane.

Moreover, while the test method described in PTL 1 carries out CHF under coagulation conditions in a closed system, the amounts of filtrate and replacement fluid are constant, which precludes testing with increased drainage. It also cannot be applied to the modes of CHD or CHDF (pre-dilution and post-dilution) that are commonly employed in the clinic.

CITATION LIST

Patent Literature

[PTL 1] Japanese Unexamined Patent Publication No. 2016-123711

Non-Patent Literature

[NPL 1] Performance evaluation methods for blood purification devices 2012, Journal of the Japanese Society for Dialysis Therapy 45(5): 435-445, 2012

SUMMARY

Technical Problem

In light of the prior art described above, the problem to be solved by the invention is to provide a closed circulation test apparatus for a blood purification device that allows fluid volume such as dialysate to be independently (freely) set in each mode of CHF, CHD and CHDF (pre-dilution and post-dilution), that facilitates management of multiple pump operation, and that makes possible "evaluation of removal performance for blood waste products" and "evaluation of membrane life performance".

Solution to Problem

The present inventors have completed this invention upon finding, unexpectedly, that by providing a replacement fluid container (7) in the closed circulation test apparatus of a blood purification device it is possible to obtain a test apparatus that allows the volume of fluid such as of dialysate to be freely set in each mode of CHF, CHD and CHDF (pre-dilution and post-dilution), that can facilitate management of multiple pump operation, and that makes possible "evaluation of removal performance for blood waste products" and "evaluation of membrane life performance".

Specifically, the present invention provides the following.

[1] A closed circulation test apparatus (14) for performance evaluation testing of a blood purification device (1) in a closed circuit in a state of non-contact with air, in which the blood purification device (1), a blood bag (2) and a replacement fluid container (7) are set, the closed circulation test apparatus (14) comprising:
  a blood supply line (3) that sends blood from the blood bag (2) to the blood purification device (1) via a blood pump (5);
  a blood return line (4) that sends blood that has left the blood purification device (1) to the blood bag (2) via resistance means (6);
  a filtrate line (8) that sends filtrate that has left through a dialysate outlet (1b) of the blood purification device (1) to the replacement fluid container (7) via a filtrate pump (9); and
  a dialysate line (10) that sends dialysate or replacement fluid from the replacement fluid container (7) to a dialysate inlet (1a) and/or the blood return line (4) of the blood purification device (1) via a dialysate pump (11).

Advantageous Effects of Invention

The closed circulation test apparatus for a blood purification device of the invention independently (freely) sets volumes of dialysate, for example, in each mode of CHF, CHD and CHDF (pre-dilution and post-dilution), facilitates management of multiple pump operation, and simultaneously makes possible "evaluation of removal performance for blood waste products" and "evaluation of membrane life performance" with a blood purification device.

DESCRIPTION OF EMBODIMENTS

Figure 1:
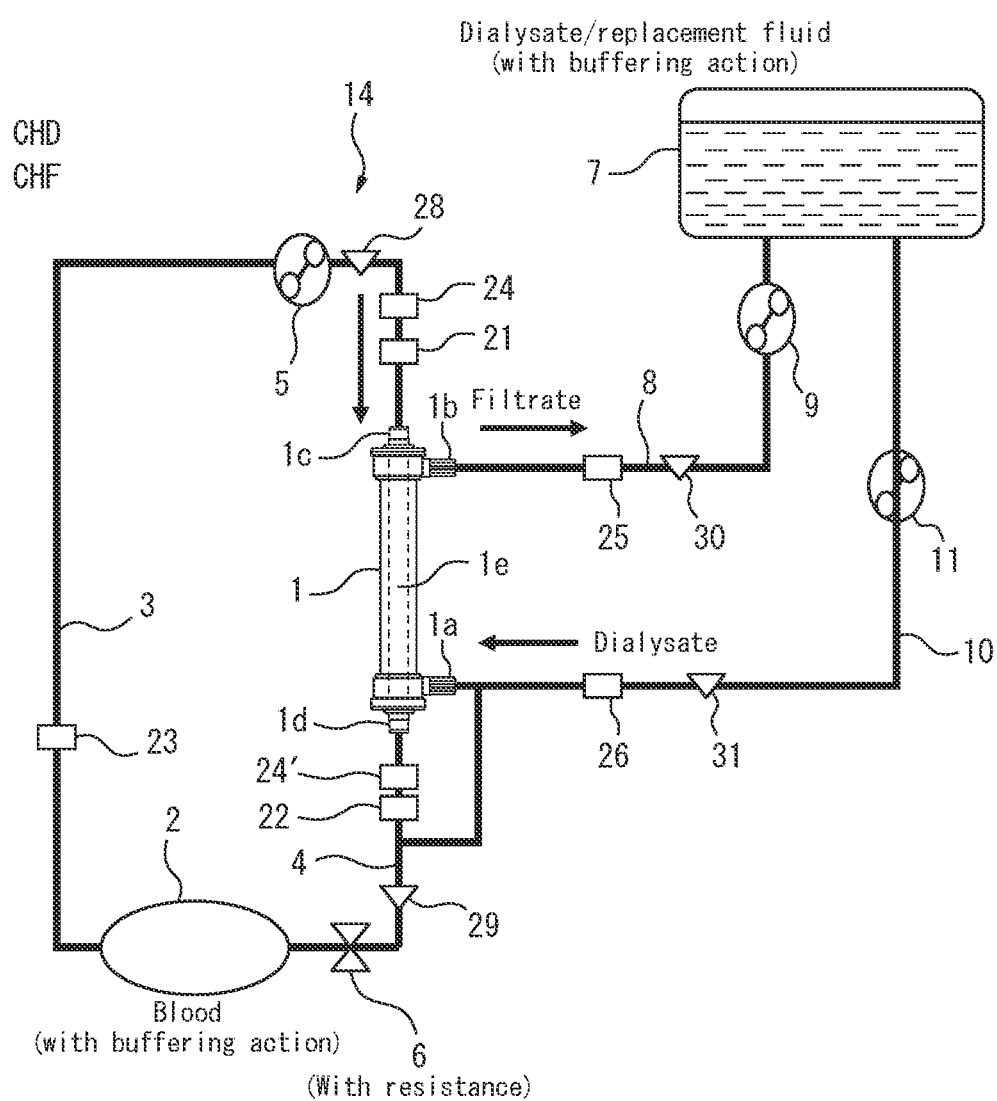
FIG. 1 is an example of a closed circulation test apparatus in a blood purification device according to an embodiment of the invention.

An embodiment of the invention will now be described in detail.

One embodiment of the invention is a closed circulation test apparatus (14) for performance evaluation testing of a blood purification device (1) in a closed circuit in a state of non-contact with air, in which the blood purification device (1), a blood bag (2) and a replacement fluid container (7) are set, the closed circulation test apparatus (14) comprising:

a blood supply line (3) that sends blood from the blood bag (2) to the blood purification device (1) via a blood pump (5);

a blood return line (4) that sends blood that has left the blood purification device (1) to the blood bag (2) via resistance means (6);

a filtrate line (8) that sends filtrate that has left through a dialysate outlet (1b) of the blood purification device (1) to the replacement fluid container (7) via a filtrate pump (9); and a dialysate line (10) that sends dialysate or replacement fluid from the replacement fluid container (7) to a dialysate inlet (1a) and/or the blood return line (4) of the blood purification device (1) via a dialysate pump (11).

FIG. 1 shows an example of a closed circulation test apparatus in a blood purification device according to this embodiment. In FIG. 1, the closed circulation test apparatus (14) is configured as a test circuit that can comparatively evaluate membrane life performance (lifetime and fouling, antithrombogenicity, etc.) for a blood purification device (1) that separates waste products in blood during filtration or dialysis of blood, under essentially the same conditions of blood flow and blood pressure, and filtrate volume or drainage as during actual use, but in a non-clinical setting in which it is not used for a patient.

According to this embodiment, the closed circulation test apparatus (14) used is for comparative testing of membrane life performance of different hemofiltration devices, where the blood purification device (1) to be tested with the closed circulation test apparatus (14) is a hemofiltration device that filters blood during treatment by continuous hemofiltration (CHF). The closed circulation test apparatus (14) is not limited to usage for testing of a hemofiltration device, incidentally, and it may also be used for testing of different types of blood purification devices such as a hemodialysis device used for dialysis (CHD).

The blood purification device (1) used for this embodiment is one having a publicly known construction comprising mainly an inlet port (1c) as the inlet for blood removed from a patient, a hollow membrane (1e) comprising a plurality of bundled hollow fiber membranes through which blood that has flowed in from the inlet port (1c) passes, an outlet port (1d) as an outlet for blood that has passed through the hollow membrane (1e) to leave the device, an inlet port (or "dialysate inlet") (1a) as an inlet for dialysate to the outside of the hollow fiber membrane, and a purification port (or "dialysate outlet") (1b) as a discharge port for waste product-containing fluid and/or an outlet for dialysate that has permeated to the outside of the hollow fiber membrane.

The closed circulation test apparatus (14) is constructed as a closed circuit through which test fluid flows in circulation via the blood purification device (1) in non-contact with air, and it is provided within the blood supply line (3) and blood return line (4) and the blood supply line (3) or blood return line (4) through which test fluid (blood) flows, and comprises resistance means (6) to match the flow rate and pressure of the test fluid (blood) in the blood supply line (3) and blood return line (4) to an actual use environment.

For this embodiment, the test fluid used is not limited to human blood (whole blood), and may be another fluid having blood components similar to human blood, such as animal blood or artificial blood. A fluid that is blood diluted with physiological saline may also be used.

Each line (i.e. blood circuit) used in the closed circulation test apparatus (14) of the blood purification device is made of a polyvinyl chloride tube, though this is not limitative. It may have a length and diameter such that the total volume of test fluid housed inside the blood supply line (3) and blood return line (4) is approximately 150 mL.

The closed circulation test apparatus (14) includes a filtrate line (8) that is connected to the dialysate outlet (1b) as a discharge port for waste product-containing fluid that has permeated to the outside of the hollow membrane (1e) of the blood purification device (1) and/or an outlet for dialysate, and sends waste product-containing fluid that has permeated to the outside of the hollow fiber membrane and/or filtrate that has passed through to the outside of the hollow fiber membrane, to the replacement fluid container (7) via the filtrate pump (9), and a dialysate line (10) that is connected to the replacement fluid container (7) and sends dialysate or replacement fluid to the dialysate inlet (1a) (CHD) or blood return line (4) (CHF) via the dialysate pump (11). Transfer of dialysate or replacement fluid to the dialysate inlet (1a) (CHD) or blood return line (4) (CHF) via the dialysate pump (11) can be accomplished using a three-way valve (not shown), for example.

Figure 2:
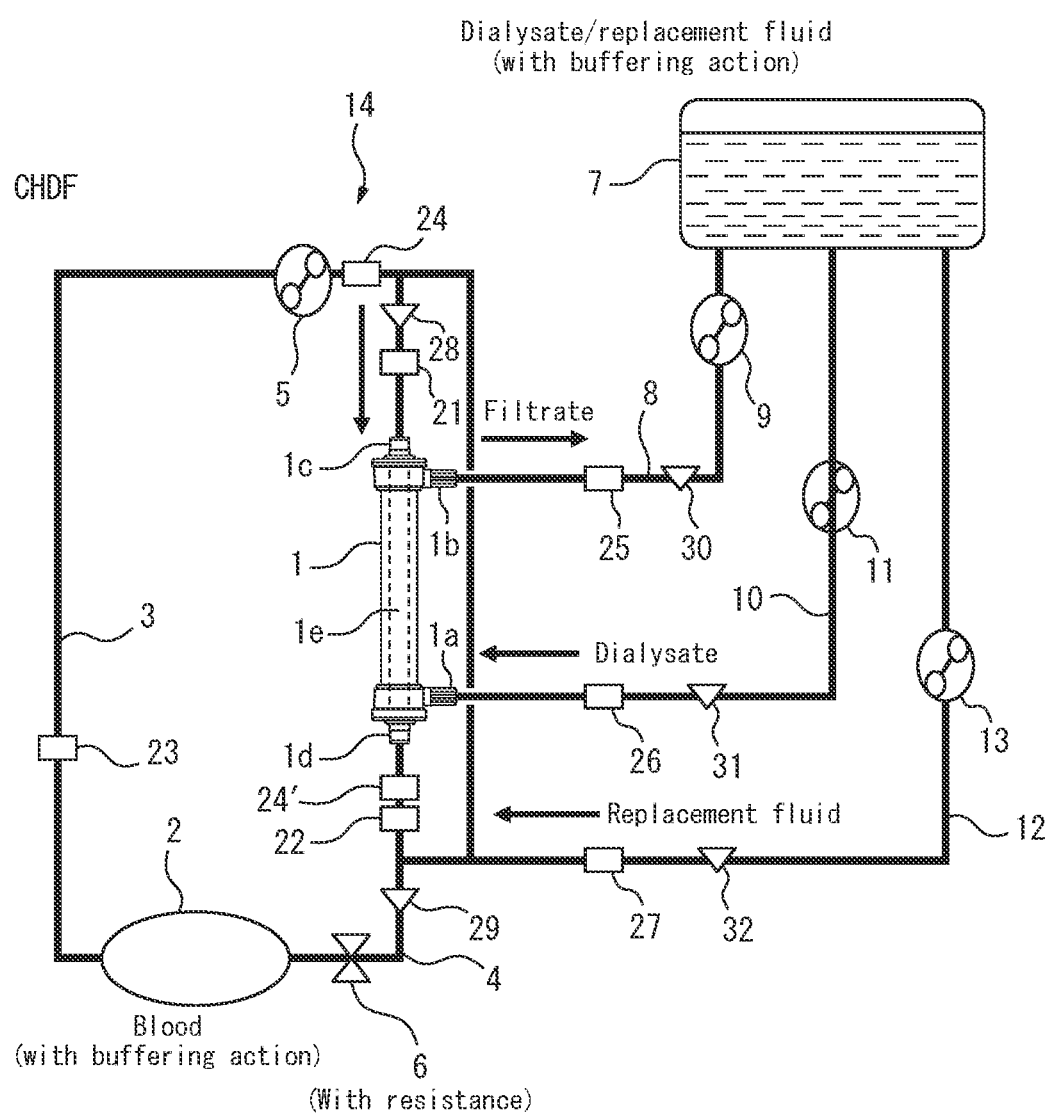
FIG. 2 is another example of a closed circulation test apparatus in a blood purification device according to an embodiment of the invention.

Another embodiment of the invention is a closed circulation test apparatus (14) which further comprises a replacement fluid line (12) that sends dialysate or replacement fluid from the replacement fluid container (7) to the blood supply line (3) and/or blood return line (4) via a replacement fluid pump (13) (CHDF) (see FIG. 2). The line for feeding from the replacement fluid pump (13) to the blood supply line (3) simulates pre-dilution in CHDF, and the line for feeding from the replacement fluid pump (13) to the blood return line (4) simulates post-dilution in CHDF. Transfer to the blood supply line (3) and/or blood return line (4) via the replacement fluid pump (13) can be accomplished using a three-way valve (not shown), for example.

By providing the replacement fluid container (7) in the closed circulation test apparatus of the blood purification device, the blood purification device (1) can be used for filtration and/or water removal from test fluid (blood).

According to the one embodiment shown in FIG. 1, the replacement fluid container (7) may be provided in the closed circulation test apparatus (14) of the blood purification device to allow operation of the filtrate pump (9) and dialysate pump (11) in tandem. Water removal may be set so that the flow rate for flow through the filtrate line (8) is greater than the flow rate for flow through the dialysate line (10).

According to another embodiment shown in FIG. 2, the replacement fluid container (7) may be provided in the closed circulation test apparatus (14) of the blood purification device to allow operation of three pumps: the filtrate pump (9), dialysate pump (11) and replacement fluid pump (13), in tandem. Water removal may be set so that the flow rate for flow through the filtrate line (8) is greater than the total flow rate for flow through the dialysate line (10) and replacement fluid line (12).

The fluid volume in the blood bag (2) is not particularly restricted but is preferably 200 mL or greater. If the fluid volume in the blood bag (2) is less than 200 mL, then the fluid volume in the blood bag (2) will tend to be insufficient and may hamper circulation during water removal for the other embodiment of the invention. The blood in the blood bag (2) is also preferably stirred as appropriate using a stirrer or shaker so that the blood cell components do not precipitate downward.

The fluid volume in the replacement fluid container (7) is preferably 100 mL or greater. If the fluid volume in the replacement fluid container (7) is less than 100 mL, then the fluid volume in the replacement fluid container (7) will tend to be insufficient and may hamper circulation during operation of the closed circulation test apparatus (14) of the blood purification device for the other embodiment of the invention.

The resistance means (6) is provided in the blood supply line (3) or blood return line (4). The resistance means (6) in FIGS. 1 and 2 is provided in the blood return line (4).

The blood supply line (3) and blood return line (4) are provided with pressure gauges (21 to 23), allowing constant measurement of the ingoing pressure and outgoing pressure in the blood purification device (1). The filtrate line (8), dialysate line (10) and replacement fluid line (12) are also provided with pressure gauges (25 to 27), allowing constant measurement of the outgoing pressure in each line.

The blood supply line (3), blood return line (4), filtrate line (8), dialysate line (10) and replacement fluid line (12) are provided with flow meters (28 to 32), allowing confirmation that the fluid in each line is flowing at the rate set by the pumps.

In order to set the temperature of each fluid in the apparatus, the closed circulation test apparatus (14) of the blood purification device is also provided with temperature control means for adjusting the temperature of the blood purification device (1), blood bag (2), replacement fluid container (7) and the entire apparatus. An example is temperature control means comprising a water tank with water stored inside it, and a heater that keeps the water temperature in the water tank at a predetermined temperature. By placing the blood bag (2) and a portion of the blood supply line (3) in the water tank, it is possible to keep the test fluid flowing through the blood supply line (3) and blood return line (4) at a constant temperature similar to human body temperature (about 36 to 37° C.). Similarly, by placing the replacement fluid container (7) and portions of the filtrate line (8), dialysate line (10) and replacement fluid line (12) in the water tank, it is possible to keep the dialysate or replacement fluid flowing through the filtrate line (8), dialysate line (10) and replacement fluid line (12) at a constant temperature similar to human body temperature (about 36 to 37° C.).

The entire closed circulation test apparatus (14) of the blood purification device may also be placed in a closed space, and the temperature control means may comprise a heater that maintains the closed space at a predetermined temperature.

Each constituent element of the closed circulation test apparatus (14) of the blood purification device is in a positional relationship producing a level difference that simulates the effects of differential pressure due to level differences of each device provided in the blood circuit in a blood purification apparatus used for actual blood filtration, while also taking into account the effect of gravity by the level difference. While not limitative, the blood bag (2) is preferably situated at approximately half the height of the blood purification device (1), and the height position of the replacement fluid container (7) is also preferably between 700 mm above and 700 mm below the height of the blood bag (2).

In the embodiment shown in FIG. 1 and FIG. 2, the blood flow through the blood supply line (3) or the filtration volume through the filtrate line (8), and the dialysis volume through the dialysate line (10) are not particularly restricted, but in order to simulate clinical CRRT therapy, the blood flow through the blood supply line (3) is preferably 50 mL/min to 150 mL/min, and the total of the filtration flow rate through the filtrate line (8) and the dialysis volume through the dialysate line (10) is preferably 500 mL/hr to 1500 mL/hr.

For the embodiment shown in FIG. 1 and FIG. 2, the blood pump (5), filtrate pump (9), dialysate pump (11) and replacement fluid pump (13) may be but are not limited to roller pumps, and they may be substituted by other types of pumps so long as they can be driven. The resistance means (6) has a construction with a clamp that imparts aperture resistance to the blood return line (4) to simulate peripheral resistance in the human body, but this is not limitative and various substitute devices such as valves may be used instead, so long as a similar effect is exhibited. The resistance means (6) functions as a vein model to adjust the flow of test fluid to simulate a human vein.

Blood collection ports (24, 24') are used to harvest samples of test fluid during testing. In FIG. 1 and FIG. 2, the blood collection port (24) is set in the blood supply line (3), but this is not limitative and it may instead be set in the blood return line (4) (blood collection port (24')).

The following is an evaluation test method for evaluating the blood waste product removal performance and membrane fouling of the blood purification device (1) using the closed circulation test apparatus (14) of the blood purification device.

Another embodiment of the invention is a method for evaluating the blood waste product removal performance and membrane fouling of a blood purification device by adjusting the fluid volume of dialysate, for example, in the closed circulation test apparatus (14) of the blood purification device.

The blood purification device (1) to be tested is set in the closed circulation test apparatus (14) of the blood purification device, and the test fluid (blood) is filled into the blood supply line (3) and blood return line (4). Dialysate or replacement fluid are filled into the filtrate line (8) and dialysate line (10). The dialysate or replacement fluid are filled into the replacement fluid line (12) when the replacement fluid line (12) is used.

The blood pump (5), filtrate pump (9) and dialysate pump (11) are driven. When the replacement fluid line (12) is used, the replacement fluid pump (13) is driven.

Blood with a pulsatile flow created by the blood pump (5) under the conditions similar to an actual use environment passes from the blood bag (2) to the blood pump (5), and flows from the inlet port (1c) of the blood purification device (1) through the hollow membrane (1e) inside it. The blood that has passed through the hollow membrane (1e) flows from the blood outlet port (1d) to the blood return line (4) and through the resistance means (6), returning to the blood bag (2).

During the test, blood is harvested as a sample from the blood collection port (24, 24') and various components in it are measured, while data relating to periodic changes in the components is also obtained. The data can be used to evaluate removal performance of blood waste products by the blood purification device (1) by calculating the clearance by the method described in NPL 1, for example.

During the test, the membrane life performance of the blood purification device (1) can be evaluated by its lifetime. The blood pump (5) is driven continuously for a time corresponding to a period in an actual use environment (for example, about 3 hours to 3 days). The pressure gauges 21 to 23 and 25 to 27 and the flow meters 28 to 32 are periodically monitored during this time, and data relating to periodic changes in the inlet pressure, outlet pressure or their differential pressure in the blood purification device (1) are acquired. The lifetime of the blood purification device (1) can be determined based on the acquired data. When the inlet pressure of the blood purification device (1) has increased to a predetermined value (such as 150 mmHg) from the initial value (70 mmHg, for example), even if the driving time has not elapsed, the blood pump (5), filtrate pump (9), dialysate pump (11) and replacement fluid pump (13) are stopped and the test is completed, and the elapsed time from the start of the test is also acquired as data.

During the test, the membrane life performance of the blood purification device (1) can also be evaluated by clogging (fouling) of the dialysis membrane. For example, it can be evaluated using the ultrafiltration rate, calculated as "drainage/(transmembrane pressure (TMP)/dialysis time)". The TMP represents the pressure difference between the blood side and dialysate side.

After completion of the test, the life performance of the blood purification device (1) can be evaluated based on antithrombogenicity. The antithrombogenicity can be evaluated by the method described in PTL 1, for example. This method allows evaluation of periodic thrombus formation in the hollow fiber membrane as the blood flow path, and clogging of the blood flow path caused by the thrombus formation.

According to this embodiment, therefore, a particular, notable and advantageous effect is exhibited whereby an evaluation test can be carried out for a blood purification device while maintaining the desired flow rate and pressure and test fluid components without contact with air, and a test that is essentially the same as under actual use conditions with a patient is carried out in a non-clinical setting without a patient.

Incidentally, the constructions of the parts (elements) of the apparatus of the invention are not limited to those depicted in the attached drawings and may incorporate various modifications so long as essentially the same effect is exhibited.

INDUSTRIAL APPLICABILITY

The closed circulation test apparatus for a blood purification device of the invention independently (freely) sets fluid volumes of dialysate and the like and facilitates management of multiple pump operation, and it can therefore be suitably used for "evaluation of removal performance for blood waste products" and "evaluation of membrane lifetime performance".

REFERENCE SIGNS LIST

1 Blood purification device
1a Dialysate inlet
1b Dialysate outlet
1c Inlet port
1d Outlet port
1e Hollow fiber membrane
2 Blood bag
3 Blood supply line
4 Blood return line
5 Blood pump
6 Resistance means
7 Replacement fluid container
8 Filtrate line
9 Filtration pump
10 Dialysate line
11 Dialysate pump
12 Replacement fluid line
13 Replacement fluid pump
14 Closed circulation test apparatus of blood purification device
21 Pressure gauge
22 Pressure gauge
23 Pressure gauge
24 Blood collection port
24' Blood collection port
25 Pressure gauge
26 Pressure gauge
27 Pressure gauge
28 Flow meter
29 Flow meter
30 Flow meter
31 Flow meter
32 Flow meter

The invention claimed is:

1. A closed circulation test apparatus for performance evaluation testing of a blood purification device in a closed circuit in a state of non-contact with air, in which the blood purification device, a blood bag and a replacement fluid container are set, the closed circulation test apparatus comprising:
   a blood supply line that sends blood from the blood bag to the blood purification device via a blood pump;
   a blood return line that sends blood that has left the blood purification device to the blood bag via resistance device;
   a filtrate line that sends filtrate that has left through a dialysate outlet of the blood purification device to the replacement fluid container via a filtrate pump; and
   a dialysate line that sends dialysate or replacement fluid from the replacement fluid container to a dialysate inlet and/or the blood return line of the blood purification device via a dialysate pump.

2. The closed circulation test apparatus according to claim 1, which further comprises:
   a replacement fluid line that sends dialysate or replacement fluid from the replacement fluid container to the blood supply line and/or blood return line via a replacement fluid pump.

3. A method allowing simultaneous evaluation of removal performance for blood waste products and evaluation of membrane lifetime performance with a blood purification device, wherein the flow rates of dialysate, filtrate and replacement fluid are independently set and adjusted in a closed circulation test apparatus according to claim 2.

4. The method according to claim 3, which is carried out under water removal conditions where the flow rate of filtrate is greater than the total flow rate of dialysate and replacement fluid.

5. A method allowing simultaneous evaluation of removal performance for blood waste products and evaluation of membrane lifetime performance with a blood purification device, wherein the flow rates of dialysate, filtrate and replacement fluid are independently set and adjusted in a closed circulation test apparatus according to claim 1.

6. The method according to claim 5, which is carried out under water removal conditions where the flow rate of filtrate is greater than the total flow rate of dialysate and replacement fluid.

* * * * *